United States Patent [19]  [11] 4,137,417
Hazama  [45] Jan. 30, 1979

[54] PROCESS FOR PRODUCING AN ENAMIDE

[75] Inventor: Motoo Hazama, Kyoto, Japan

[73] Assignee: Sumitomo Chemical Company, Limited, Osaka, Japan

[21] Appl. No.: 790,908

[22] Filed: Apr. 26, 1977

[30] Foreign Application Priority Data

Apr. 30, 1976 [JP] Japan ................................. 51-50537

[51] Int. Cl.$^2$ ..................... C07C 102/00; C07C 67/00
[52] U.S. Cl. ................................... 560/250; 252/472;
260/326.13 R; 260/404; 260/465 D; 260/465.4;
260/558 R; 260/558 P; 260/561 R; 260/562 R;
260/562 P; 542/421; 560/8; 560/20; 560/22;
560/100; 560/103; 560/105; 560/106; 560/107;
560/110
[58] Field of Search ................... 560/250, 8, 103, 106,
560/107, 110, 100, 105; 252/472

[56] References Cited

U.S. PATENT DOCUMENTS 4,049,584 9/1977 Weissel ............................ 252/472 X
4,055,512 10/1977 Kageyama et al. ............. 252/472 X

OTHER PUBLICATIONS

Boar et al., Journal of the Chemical Society (1975), Perkin I, pp. 1237–1241.
Breitner et al., CA 54:3256f (1960).
Hartung et al., CA 48:115f (1952).
Theilheimer, Organic Syntheses, Abstract No. 40, vol. 14 (1958).
Albertson et al., J. Am. Chem. Soc., 70, 1150 (1948).
Hoy et al., J. Org. Chem., 23, 967 (1958).
Ferris et al., J. Org. Chem., 25, 492 (1960).

Primary Examiner—Thomas Waltz
Attorney, Agent, or Firm—Cushman, Darby & Cushman

[57] ABSTRACT

Enamides are prepared by hydrogenating oximes having at least one hydrogen atom at the α-position in the presence of a carboxylic anhydride using a ruthenium catalyst. These enamides are important to obtain amino group-containing compounds by reduction or polymerization.

5 Claims, No Drawings

PROCESS FOR PRODUCING AN ENAMIDE

The present invention relates to a process for the production of enamides. More particularly, it relates to a process for the production of enamides which comprises hydrogenating oximes having at least one hydrogen atom at the α-position in the presence of a carboxylic anhydride using a ruthenium catalyst.

Enamides are known to be useful compounds in industry. For example, they can be converted to acylamines by reduction and polymers having amino groups by polymerization. Furthermore, they can be used as intermediates for the production of amino acids. For example, acylaminoacrylic acid derivatives are converted to amino acid derivatives by reduction or directly to optically active amino acid derivatives by asymmetric reduction (Chem. Comm. 1972, 10). So far, it has been known that enamides can be produced by the following processes:

1. Reaction of nitriles with a Grignard reagent followed by acylation (Bull. Soc. Chim. Fr. 1454 (1965)),
2. Reaction of aldehydes with amides (J. Org. Chem. 26, 1097, (1961)),
3. Reaction of acetals with amides (Ber. 99, 2127, (1966)),
4. Reaction of ketones or aldehydes with ammonia in the presence of $TiCl_4$, followed by acylation (Tet. Lett. 4897, (1971)),
5. Beckmann rearrangement of α, β-unsaturated ketoximes (J. Org. Chem. 21, 520, (1956)),
6. Dehydrohalogenation of α-halogenated acylamino acids (U.S.P. 2,588,968), and
7. Elimination of carboxylic acid from N,O-diacylhydroxyl-amine derivatives. (Bull. Chem. Soc. Jap. 47, 3109 (1974)).

However, these known processes have disadvantages from a commercial point of view, that is, they are low in yield and require many reaction steps and expensive solvents or reacting agents.

It is also told that, when oximes are hydrogenated in the presence of a carboxylic anhydride using a platinum metal catalyst such as platinum, palladium or rhodium, one mole of the oximes absorbs two moles of hydrogen to produce the acylated products of a primary amine (J. Org. Chem. 25, 492, 1302 (1960); ibid 23, 967 (1958); J. Am. Chem. Soc. 70, 1150 (1948)). The inventors have found, however, that when oximes having at least one hydrogen atom at the α-position are hydrogenated in the presence of a carboxylic anhydride using a ruthenium catalyst, the absorption of hydrogen stops, unlike the case of the platinum metal catalyst, at that time when one mole of hydrogen has just been absorbed, and enamides are selectively produced in a high yield as the result of the transfer of the double bond caused by the rearrangement of the α-hydrogen atom.

An object of the present invention is to provide a process for the production of enamides of the formula (I),

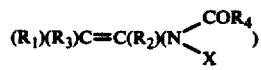

wherein $R_1$ and $R_2$ are independently a hydrogen atom, an alkyl, cycloalkyl, cycloalkylalkyl, aralkyl, aryl, cyano, acyl, carboxyl, carbamoyl, —$CONR_5R_6$ (in which $R_5$ and $R_6$ are independently an alkyl, aralkyl or aryl group) or —$ClOOR_5$ group (in which $R_5$ is as defined above), said alkyl, cycloalkyl, cycloalkylalkyl, aralkyl and aryl groups being substituted or not with a halogen atom, a cyano, imidazolyl, N-acylimidazoly, indolyl, N-acylindolyl group or one of the groups, —$COOR_5$, —$COR_5$, —$CONR_5R_6$, —$OR_5$, —$OCOR_5$, —$NR_5R_6$, —$NHCOR_5$ and —$N(COR_5)_2$, wherein $R_5$ and $R_6$ are as defined above, or $R_1$ and $R_2$, taken together, may form an alicyclic ring; $R_3$ has the same meanings as $R_2$, or $R_3$ is a hydroxyl, imidazolyl, N-acylimidazolyl, indolyl, N-acylindolyl group or one of the groups, —$COR_5$, —$OR_5$, —$OCOR_5$, —$NR_5R_6$, —$NHCOR_5$ and —$N(COR_5)_2$, wherein $R_5$ and $R_6$ are as defined above; $R_4$ is an alkyl, aralkyl or aryl group; and X is a hydrogen atom or $R_4CO$ group, which comprises hydrogenating oximes having at least one hydrogen atom at the α-position represented by the formula (II),

wherein $R_1$, $R_2$ and $R_3$ are as defined above, in the presence of a carboxylic anhydride of the formula (III),

wherein $R_4$ is as defined above, using a ruthenium catalyst.

Referring to the starting materials of the present invention, the oximes used in the present invention may be of syn-form, anti-form or mixed-form of the both. In the formulae (I), (II) and (III), the term "alkyl" preferably means a straight or branched alkyl group having 1 to 20 carbon atoms (e.g. methyl, ethyl, n-propyl, iso-propyl, n-butyl, iso-butyl, sec-butyl, tert-butyl). The term "cycloalkyl" preferably means a cycloalkyl group having 3 to 20 carbon atoms (e.g. cyclopropyl, cyclopentyl, cyclohexyl). The term "cycloalkylalkyl" preferably means the aforesaid alkyl groups substituted with the aforesaid cycloalkyl groups (e.g. cyclopropylmethyl, cyclohexylmethyl). The term "aryl" preferably means an aryl group having 6 to 20 carbon atoms (e.g. phenyl, tolyl, xylyl, cumenyl, naphthyl). The term "aralkyl" preferably means the aforesaid alkyl groups substituted with the aforesaid aryl groups (e.g. benzyl, phenethyl, naphthylmethyl). The term "acyl" means preferably —$COR_5$ wherein $R_5$ is as defined above (e.g. acetyl, propionyl, pivaloyl, benzoyl, phenylacetyl). The term "acyl" in N-acylimidazolyl and N-acylindolyl groups has the same meaning as above. The phrase "$R_1$ and $R_2$, taken together, form an alicyclic ring" means the formation of alicyclic rings having 5 to 20 carbon atoms, for example,

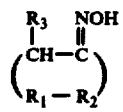

wherein —$R_1$—$R_2$— is a trimethylene, tetramethylene, pentamethylene or hexamethylene linkage.

The specific examples of the oxime are as follows: acetoxime, methyl ethyl ketoxime, cyclohexanone oxime, acetophenone oxime, propiophenone oxime, benzyl phenyl ketoxime, 1-acetonaphthoxime, propionaldoxime, ethyl 5-cyano2-oximinovalerate, ethyl 3-phenyl-2-oximinopropionate, ethyl 3-(3′,4′-acetoxyphenyl)-2-oximinopropionate, ethyl 2-oximinopropionate, methyl 4-methyl-2-oximinovalerate, propyl 3-methyl-2oximinobutyrate, 3-(3-indolyl)-2-oximinopropionic acid, ethyl 4-methoxycarbonyl-2-oximinobutyrate and the like.

When the oximes have hydrogen atoms at the α- and α′-positions, the transfer of the double bond takes place in two different ways so that the enamides are obtained as a mixture.

The specific examples of $R_4$ include a methyl, ethyl, n-propyl, isopropyl, n-butyl, sec-butyl, tert-butyl, benzyl, phenyl group and the like. These groups correspond to the acyl residues of the carboxylic anhydride used as a reacting agent.

As the specific examples of the enamide of the present invention, there may be exemplified the following compounds: 1-acetylaminocyclohexene, 1-diacetylaminocyclohexene, 2-acetylaminobutene-1, 2-diacetylaminobutene-1, 2-acetylaminobutene-2, 2-diacetylaminobutene-2, 1-phenyl-1-acetylaminopropene-1, 1-phenyl-1-diacetylaminopropene-1, 1,2-diphenyl-1-acetylaminoethylene, 1,2-diphenyl-1-diacetylaminoethylene, 1-(1-naphthyl)-1-acetylaminoethylene, 2-methyl-1-acetylaminoethylene, 2-methyl-1-diacetylaminoethylene, 1,2-diphenyl-1-acetylamino-2-acetoxyethylene, 1,2-diphenyl-1-diacetylamino-2-acetoxyethylene, 1,2-diphenyl-1-acetylamino-2-hydroxyethylene, 1,2-diphenyl-1-diacetylamino-2-hydroxyethylene, ethyl 5-cyano-2-acetylamino-1-pentenoate, ethyl 5-cyano-2-diacetylamino-1-pentenoate, ethyl 5-cyano-2-benzoylamino-1-pentenoate and the like.

The method how to carry out the present invention will be explained hereinafter.

As the carboxylic anhydrides used as a reacting agent, there may be exemplified acetic anhydride, propionic anhydride, butyric anhydride, isobutyric anhydride, valeric anhydride, isovaleric anhydride, pivalic anhydride, phenylacetic anhydride, benzoic anhydride and the like. These carboxylic anhydrides should be used in an amount of at least 2 times by mole based on the oxime and they may be used in a large amount as a reacting agent combined with a solvent.

Ruthenium as a catalyst is used in the form of an oxide (e.g. $RuO_2$) or metallic ruthenium and may be supported on a suitable carrier (for example Ru-carbon, Ru-alumina). The amount of the catalyst used is 0.001 to 100% by mole, practically 0.01 to 10% by mole, based on the oxime. These catalysts are commercially available from Engelhald Industries Newark N.J.

The process of the present invention is usually carried out in a solvent. As the solvent, there may be used the carboxylic anhydrides as a reacting agent or solvents not disturbing the reaction. Examples of preferred solvent are aromatic hydrocarbons (e.g. benzene, toluene, xylene), aliphatic hydrocarbons (e.g. hexane, cyclohexane), lower carboxylic acids (e.g. acetic acid, propionic acid) and mixtures thereof. The reaction of the present invention is carried out at more than 0° C. Too low reaction temperatures lower the rate of reaction, while too high ones lead to the production of by-products. Consequently, reaction temperatures between 20° C. and 120° C. are preferred. The hydrogenation proceeds under a hydrogen pressure corresponding to atmospheric one but a suitable pressure such as 1 to 200 atm. may be applied.

The present invention will be explained in more detail with reference to the following examples, however the present invention is not limited thereto.

EXAMPLE 1

1.13 g (10 mmole) of cyclohexanone oxime was dissolved in 20 ml of acetic anhydride and 200 mg (0.1 mmole) of the 5 % Ru-carbon catalyst was added thereto. Hydrogenation was carried out at 100° C. at 1 atm. The absorption of hydrogen stopped at that time when an equimolar amount (240 ml) of hydrogen was just absorbed. After the catalyst was filtered off, the filtrate was concentrated under reduced pressure. The residue was chromatographed on silica gel to obtain 0.12 g (yield 25.8 %) of 1-acetylaminocyclohexene and 1.04 g (yield 57.5 %) of 1-diacetylaminocyclohexene.

EXAMPLES 2 to 6

The reactions were carried out in the same manner as in Example 1 except that the different kinds of oxime were used as a starting material. The results are shown in Table 1.

Table 1

| Example | Material | Products (yield %) | |
|---|---|---|---|
| 2 | Propiophenone oxime | 1-phenyl-1-acetylaminopropene-1 | (26.9) |
|  |  | 1-phenyl-1-diacetylaminopropene-1 | (54.8) |
| 3 | Benzyl phenyl ketoxime | 1,2-diphenyl-1-acetylaminoethylene | (62.5) |
|  |  | 1,2-diphenyl-1-diacetylaminoethylene | (31.2) |
| 4 | 1-Acetonaphthoxime | 1-(1-naphthyl)-1-acetylaminoethylene | (70.5) |
| 5 | Propionaldoxime | 1-acetylaminopropene-1 | (10.5) |
|  |  | 1-diacetylaminopropene-1 | (23.2) |
|  |  | 2-acetylaminobutene-1 | ( 2.5) |
| 6 | Methyl ethyl ketoxime | 2-diacetylaminobutene-1 | ( 4.1) |
|  |  | 2-acetylaminobutene-2 | ( 5.3) |
|  |  | 2-diacetylaminobutene-2 | (10.2) |

EXAMPLE 7

2.27 g (10 mmole) of benzoinoxime was dissolved in 20 ml of acetic anhydride and 200 mg of the 5 % Ru-carbon catalyst was added thereto. Hydrogenation was carried out at 100° C. at 1 atm. The reaction mixture was treated in the same manner as in Example 1 to obtain 0.42 g (14.4 %) of 1,2-diphenyl-1-acetylamino-2-acetoxyethylene, 0.62 g (18.4 %) of 1,2-diphenyl-1-diacetylamino-2-acetoxyethylene, 0.38 g (12.9 %) of α-acetylaminodeoxybenzoin and 0.65 g (33.3 %) of α-diacetylaminodeoxybenzoin.

The latter two compounds are keto-isomers of 1,2-diphenyl-1-acetylamino-2-hydroxyethylene and 1,2-diphenyl-1-diacetylamino-2-hydroxyethylene, respectively.

EXAMPLE 8

1.84 g (10 mmole) of ethyl 5-cyano-2-oximinovalerate was dissolved in 20 ml of acetic anhydride and 200 mg (0.1 mmole) of the 5 % Ru-carbon catalyst was added thereto. Hydrogenation was carried out at 100° C. at 1 atm. The absorption of hydrogen stopped at that time when an equimolar amount of hydrogen was just absorbed. The reaction mixture was treated in the same manner as in Example 1 to obtain 1.26 g (yield 59.5 %)

of ethyl 5-cyano-2-acetylamino-1-pentenoate (m.p. 103.1° C.).

Elemental analysis (as $C_{10}H_{14}N_2O_3$):

|  | C | H | N |
|---|---|---|---|
| Calcd. | 57.13 | 6.71 | 13.32 |
| Found | 57.07 | 6.71 | 13.19 |

IR 2250 cm$^{-1}$ ($\nu$ CN), 1720, 1680, 1660 cm$^{-1}$ ($\nu$ CO, ester, amide)
NMR CDCl$_3$ $\tau$ 1.7 (b.s, 1H, NH), 2.85 (m, 1H, CH), 5.40 (q, J=7Hz, 2H, CH$_2$), 7.23 (m, 4H, CH$_2$), 7.70 (s, 3H, CH$_3$, CO), 8,57 (t, J=7Hz, 3H, CH$_3$)

0.76 Gram (yield 31.0 %) of ethyl 5-cyano-2-diacetylamino-1-pentenoate was also obtained as an oily substance.

Elemental analysis (as $C_{12}H_{16}N_2O_4$):

|  | C | H | N |
|---|---|---|---|
| Calcd. | 57.13 | 6.39 | 11.10 |
| Found | 57.08 | 6.41 | 11.13 |

IR 2250 cm$^{-1}$ ($\nu$ CN),
1730, 1710, 1670 cm$^{-1}$ ($\nu$ CO, ester, amide)
NMR CDCl$_3$ $\tau$ 2.9 (m, 1H, CH), 5.73 (q, 2H, CH$_2$) 7.43 (m, 4H, CH$_2$), 7.63 (s, 6H, CH$_3$CO), 8.70 (t, 3H, CH$_3$)

EXAMPLES 9 to 11

The reactions were carried out in the same manner as in Example 8 except that the following reaction conditions were used. The results are shown in Table 2.

Table 2

| Example | Solvent | Acetic anhydride (g) | Pressure (atm) | NC(CH$_2$)$_2$CH=C(NHAc)(COOEt) yield (%) | NC(CH$_2$)$_2$CH=C(NAc$_2$)(COOEt) yield (%) |
|---|---|---|---|---|---|
| 9 | Acetic acid | 2.02 | 1 | 44.8 | — |
| 10 | Toluene | 2.02 | 50 | 65.5 | — |
| 11 | Acetic anhydride | 20 | 50 | 77.1 | 5.1 |

EXAMPLE 12

The reaction was carried out in the same manner as in Example 9 except that benzoic anhydride was used in place of acetic anhydride. Thus, 0.81 g (yield 30 %) of ethyl 5-cyano-2-benzoylamino-1-pentenoate was obtained.

What is claimed is:

1. A process for the production of an enamide of the formula (I),

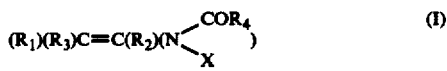

where R$_1$ and R$_2$ independently are hydrogen, alkyl or aryl or R$_1$ and R$_2$ together are cycloalkyl, R$_3$ is — OCOR$_5$, R$_5$ is alkyl, aralkyl or aryl, X hydrogen or — COR$_4$ and R$_4$ is alkyl or aryl, which comprises hydrogenating an oxime having at least one hydrogen atom at the α-position represented by the formula (II),

wherein R$_1$, R$_2$ and R$_3$ are as defined above, in the presence of a carboxylic anhydride of the formula (III).

wherein R$_4$ is as defined above, using a ruthenium catalyst, the amount of said carboxylic anhydride used being at least two times by mole based on the oxime.

2. The process according to claim 1, wherein said ruthenium catalyst is Ru-carbon or Ru-alumina and is used in the amount of 0.001 to 100 % by mole based on the oxime of the formula (II).

3. The process according to claim 2 wherein the hydrogenation is carried out at a reaction temperature of 20° to 120° C. and at a hydrogen pressure of 1 to 200 atm.

4. A process according to claim 1 wherein the starting oxime is benzoinoxime.

5. A process according to claim 1 for preparing 1,2-diphenyl-1-acetylamino-2-acetoxyethylene or 1,2-diphenyl-1-diacetylamino-2-acetoxyethylene comprising reacting benzoinoxime with acetic anhydride using Ru-carbon catalyst.

* * * * *